(12) United States Patent
Westermayer et al.

(10) Patent No.: US 10,442,750 B2
(45) Date of Patent: Oct. 15, 2019

(54) METHOD FOR PRODUCING VINYL ACETATE

(71) Applicant: WACKER CHEMIE AG, Munich (DE)

(72) Inventors: Heribert Westermayer, Burghausen (DE); Harald Michl, Mühldorf (DE); Johann Wagner, Burgkirchen a. d. Alz (DE)

(73) Assignee: WACKER CHEMIE AG, München (DE)

( * ) Notice: Subject to any disclaimer, the term of this patent is extended or adjusted under 35 U.S.C. 154(b) by 0 days.

(21) Appl. No.: 16/319,940

(22) PCT Filed: Mar. 31, 2017

(86) PCT No.: PCT/EP2017/057735
§ 371 (c)(1),
(2) Date: Jan. 23, 2019

(87) PCT Pub. No.: WO2017/174463
PCT Pub. Date: Oct. 12, 2017

(65) Prior Publication Data
US 2019/0218167 A1    Jul. 18, 2019

(30) Foreign Application Priority Data
Apr. 4, 2016 (DE) .................. 10 2016 205 487

(51) Int. Cl.
| | | |
|---|---|---|
| C07C 67/055 | (2006.01) | |
| C07C 67/54 | (2006.01) | |
| C07C 69/15 | (2006.01) | |

(52) U.S. Cl.
CPC ............ C07C 67/055 (2013.01); C07C 67/54 (2013.01); C07C 69/15 (2013.01)

(58) Field of Classification Search
None
See application file for complete search history.

(56) References Cited

U.S. PATENT DOCUMENTS

| | | | |
|---|---|---|---|
| 4,156,632 A | 5/1979 | Roscher | |
| 4,818,347 A * | 4/1989 | Roscher | C07C 67/055 203/42 |
| 5,066,365 A | 11/1991 | Roscher | |
| 2007/0032678 A1 | 2/2007 | Stamm | |
| 2016/0046557 A1 | 2/2016 | Guenaltay | |
| 2016/0311752 A1 | 10/2016 | Dafinger | |

FOREIGN PATENT DOCUMENTS

| | | |
|---|---|---|
| DE | 1278430 B | 5/1974 |
| DE | 2610624 C2 | 2/1985 |
| DE | 3422575 A1 | 12/1985 |
| DE | 102013205492 A1 | 10/2014 |
| EP | 0423658 A2 | 4/1991 |
| EP | 1760065 A1 | 3/2007 |
| GB | 1193537 A | 6/1970 |
| WO | WO14036132 A1 | 3/2014 |
| WO | WO15082450 A1 | 6/2015 |

* cited by examiner

*Primary Examiner* — Clinton A Brooks
*Assistant Examiner* — Kofi Adzamli

(57) ABSTRACT

The invention relates to a method for producing vinyl acetate, said method being characterized in that a) the gaseous product mixture leaving the reactor is cooled to a temperature of 100° C. to 120° C. using one or more heat exchangers, b) the thus obtained product mixture is supplied to a distillation column which is equipped with filling elements (pre-dehydration column), c) the pre-dehydration column head product which substantially contains wafer, vinyl acetate, and ethylene is cooled, and the condensate (head product condensate) produced in the process is separated into a water phase and an organic phase (vinyl acetate phase), which substantially comprises vinyl acetate, in a phase separator, d) at least 99 wt. % of the acetic acid contained in the product mixture is separated via the bottom of the pre-dehydration column, and the head product of the pre-dehydration column contains <0.1 wt. % of acetic acid, measured in the water phase of the head product condensate, e) the ethyl acetate contained in the product mixture is separated via the bottom of the pre-dehydration column in such a quantity that the head product of the pre-dehydration column contains <600 wt. ppm ethyl acetate, measured in the vinyl acetate phase of the head product condensate, f) 70 to 100 wt. % of the vinyl acetate phase is recirculated into the pre-dehydration column, and g) a product mixture is drawn at the bottom of the pre-dehydration column, said product mixture containing 10 to 60 wt. % of vinyl acetate.

5 Claims, 1 Drawing Sheet

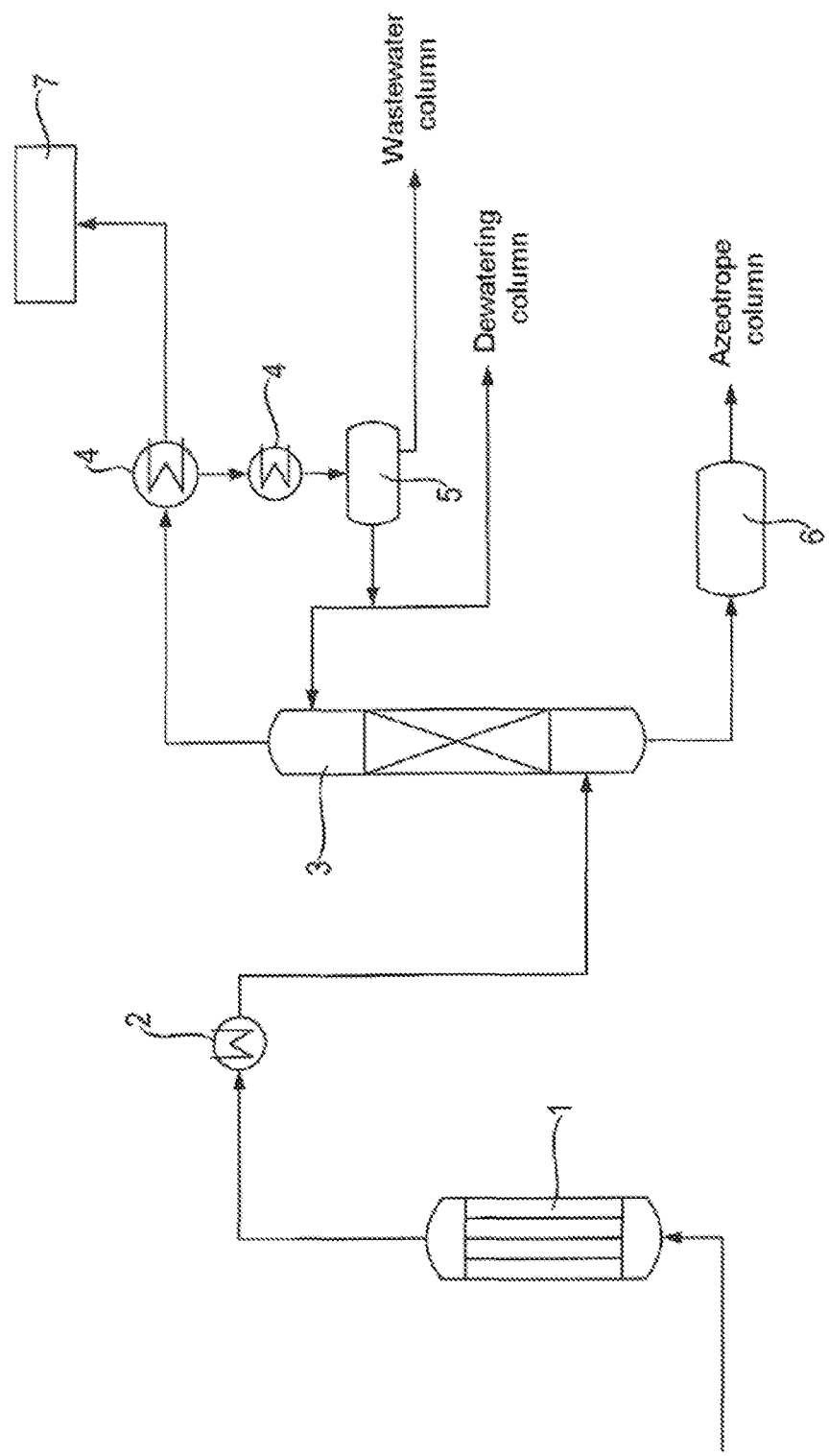

METHOD FOR PRODUCING VINYL ACETATE

CROSS-REFERENCE TO RELATED APPLICATIONS

This application is a U.S. National Phase Application of PCT/EP2017/057735, filed Mar. 31, 2017, which claims priority to German Application No. 10 2016 205 487.2 filed on Apr. 4, 2016 the contents of which are incorporated herein by reference in their entireties for all purposes.

FIELD OF THE INVENTION

The invention relates to a process for preparing vinyl acetate by means of a heterogeneously catalyzed, continuous gas-phase reaction of ethylene, acetic acid and oxygen in a reactor, where the product mixture leaving the reactor is fractionated by means of distillation.

BACKGROUND OF THE INVENTION

Vinyl acetate monomer (VAM) can be prepared in a continuous process with recirculation of the purified product stream (gas recycle process). Here, ethylene reacts with acetic acid and oxygen in a heterogeneously catalyzed gas-phase reaction over catalysts which generally contain palladium salts and alkali metal salts on a support material and may additionally be doped with gold or rhodium. Preference is given to using a Pd/Au catalyst mixture with a potassium acetate promoter.

The starting materials ethylene, oxygen and acetic acid are converted into vinyl acetate in an exothermic reaction (VAM: $\Delta_B H°_{299} = -176$ kJ/mol), generally at a gauge pressure of from 7 to 15 bar and, depending on the time on stream of the catalyst, at a temperature of generally from 130° C. to 200° C., in a fixed-bed shell-and-tube reactor or else in fluidized-bed reactors:

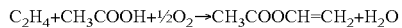

The main secondary reaction here is the total oxidation of ethylene to $CO_2$:

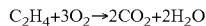

The ethylene conversion is generally from about 5% to 20%, the acetic acid conversion is from 20% to 60% and the oxygen conversion is up to 90%.

Owing to the incomplete conversion of ethylene and the secondary reactions, a gas mixture consisting predominantly of ethylene, carbon dioxide, ethane, nitrogen and oxygen (recycle gas) is circulated in the preparation of vinyl acetate. The recycle gas is admixed upstream of the fixed-bed shell-and-tube reactor with the starting materials acetic acid, ethylene and oxygen and brought to the reaction temperature by means of heat exchangers operated using hot steam. The enrichment of the recycle gas with acetic acid is usually effected by means of an acetic acid saturator heated by means of hot steam.

After the reaction, the reaction products vinyl acetate and water and unreacted acetic acid are condensed out from the recycle gas, preferably in a predewatering column, and passed to the further work-up. Starting material/product which has not been condensed out, essentially ethylene, $CO_2$ and vinyl acetate, can be taken off at the top of the predewatering column and the vinyl acetate can be scrubbed out in a scrubber operated using acetic acid (recycle gas scrubber). The overhead product from the predewatering column which has been treated in this way, namely the recycle gas, or at least part thereof, can then be freed of carbon dioxide formed in a $CO_2$ scrubber. The recycle gas is optionally compressed, replenished again with the starting materials and introduced into the reactor for gas-phase oxidation.

For the further work-up of the bottom product from the predewatering column and the bottom product from the recycle gas scrub, the product vinyl acetate and water and also unreacted acetic acid which have been condensed out can be separated from one another in a multistage distillation process which is usually operated using hot steam. The customary distillation steps for isolating the vinyl acetate and the acetic acid are azeotrope column, dewatering column, pure VAM column and also columns for residue work-up and removal of low boilers and high boilers.

DE-B 1278430 describes a process in which the product mixture leaving the reactor is fractionated in a distillation column filled with saddle bodies. At the bottom of the column, an acetic acid/water mixture which is free of vinyl acetate is taken off. The distillate obtained at the top of the column is condensed and separated into an aqueous phase and an organic phase, with the organic phase consisting of vinyl acetate, water, acetic acid and acetaldehyde being recirculated into the distillation column. A disadvantage of this process is the relatively high proportion of acetic acid in the overhead product from the column, which makes the phase separation of vinyl acetate and water difficult and therefore makes an additional separation by distillation of vinyl acetate and acetic acid and also of acetic acid and water necessary.

The process of DE-C 2610624 concerns the predewatering of the reaction mixture formed in the vinyl acetate synthesis. In this process, the product mixture is introduced into a predewatering column. A mixture of vinyl acetate, water and acetic acid is taken off from the bottom of the column. The gaseous overhead product is condensed and, after phase separation of the condensate, the organic phase is, after having been heated in a heat exchanger, recirculated into the predewatering column and the aqueous phase is passed to wastewater treatment. A disadvantage of this process is the high temperature at which the gaseous reaction mixture is transferred into the predewatering column. Measurements have shown that at relatively high entry temperatures the column surprisingly has higher ethyl acetate values at the top of the column, which makes the removal of ethyl acetate difficult. The ethyl acetate then has to be distilled off from the bottoms from the recycle gas scrubber, which is costly. In the process of DE-C 3422575 A1, too, the gas mixture leaving the reactor is, as in DE-C 2610624, introduced without prior cooling into a predewatering column, with the disadvantages just described.

EP 0423658 A2 describes a process in which the product gas mixture leaving the reactor is fed with or without cooling into the predewatering column. The process is concerned in particular with the fractional distillation of the bottom product from the recycle gas scrubber in a column which is additional compared to DE 3422575 A1. The advantage of the process is that a smaller number of column plates is needed in the work-up by distillation.

In EP 1760065 A1, the mixture leaving the reactor is introduced into a predewatering column which is constructed as tray column. A description is given of a process in which part of the bottom product from the recycle gas scrubber is recirculated to the predewatering column.

In the process described in WO 2014/036132 A1, the product gas stream from the reactor is fed into a predewatering column. A product gas stream whose composition differs from that of the product gas stream fed in is taken off from the column and is fed to a second reactor for the gas-phase oxidation. Both tray columns and packed columns are recommended as predewatering column.

BRIEF SUMMARY OF THE INVENTION

It was an object of the present invention to optimize the work-up of the product mixture obtained after the gas-phase oxidation.

The invention provides a process for preparing vinyl acetate by means of a heterogeneously catalyzed, continuous gas-phase reaction of ethylene, acetic acid and oxygen in a reactor, where the product mixture leaving the reactor is fractionated by means of distillation, the reaction products vinyl acetate and water and unreacted acetic acid are at least partly condensed out from the product mixture (recycle gas) and the recycle gas which has been treated in this way is recirculated back into the reactor, characterized in that
a) the gaseous product mixture leaving the reactor is cooled to a temperature of from 100° C. to 120° C. by means of one or more heat exchangers,
b) the resulting product mixture is fed to a distillation column which is equipped with packing elements (predewatering column),
c) the overhead product containing essentially water, vinyl acetate and ethylene from the predewatering column is cooled and the condensate obtained (overhead product condensate) is separated in a phase separator into an aqueous phase and an organic phase containing essentially vinyl acetate (vinyl acetate phase),
d) the acetic acid present in the product mixture is separated off to an extent of at least 99% by weight via the bottom of the predewatering column and the overhead product from the predewatering column contains <0.1% by weight or acetic acid, measured in the aqueous phase of the overhead product condensate,
e) the ethyl acetate present in the product mixture is separated off via the bottom of the predewatering column in such an amount that the overhead product from the predewatering column contains ≤600 ppm by weight of ethyl acetate, measured in the vinyl acetate phase of the overhead product condensate,
f) the vinyl acetate phase is recirculated to an extent of from 70 to 100% by weight into the predewatering column and
g) a product mixture containing from 10 to 60% by weight of vinyl acetate is taken off at the bottom of the predewatering column.

BRIEF DESCRIPTION OF THE DRAWINGS

FIG. 1 is a schematic of an apparatus for use in exemplary embodiments of the present invention.

DETAILED DESCRIPTION OF PREFERRED EMBODIMENTS

The process of the invention is explained in more detail below and in FIG. 1. The arrangement of the apparatuses for fractionating the product mixture from the gas-phase reaction for preparing vinyl acetate has been described many times and is known to those skilled in the art. It can also be derived from, for example, WO 2015/082450 A1.

To prepare vinyl acetate by means of a heterogeneously catalyzed, continuous gas-phase reaction of ethylene, acetic acid and oxygen, the recycle gas is loaded with fresh ethylene which replaces the proportion of ethylene consumed in the reaction and the recycle gas is fed to an acetic acid saturator. In the acetic acid saturator, generally a column having packing elements or having trays, the acetic acid which has been consumed in the reaction and that condensed out from the recycle gas is replaced by introduction of fresh acetic acid and recycled acetic acid. Oxygen is added via a nozzle to the recycle gas loaded with ethylene and acetic acid before entry into the reactor.

The recycle gas is subsequently introduced at a recycle gas pressure of preferably from 7 to 15 bar abs. into the reactor (1), preferably a fixed-bed shell-and-tube reactor made up of a cylindrical vessel in which a number of thousand, usually from 2000 to 20 000, densely packed cylindrical reaction tubes are arranged. For industrial use, tubes having a length of preferably from 5 to 10 m and an internal diameter of preferably from 25 to 40 mm are employed for this purpose. A water/steam mixture flows as heat exchange medium through the intermediate spaces between the tubes and the tubes and the wall of the vessel to effect cooling.

The tubes are charged with supported catalysts based on an inert, inorganic support material such as titanium oxide, silicon oxides, aluminum oxides which are coated with a palladium compound in combination with alkali metals and can additionally be doped with gold, rhodium or cadmium. These supported catalysts can be present in the form of spheres, cylinders or rings, with the dimensions thereof being matched to the tubes.

The reaction is generally carried out at a pressure of preferably from 7 to 15 bar abs. and at a temperature of generally from 130° C. to 200° C.

The gaseous product mixture leaving the reactor (1), which contains essentially ethylene, vinyl acetate, acetic acid, water, carbon dioxide, ethyl acetate, oxygen and inerts such as argon and nitrogen, is cooled to a temperature of from 100° C. to 120° C., preferably from 105° C. to below 115° C., by means of one or more heat exchangers (2) before entry into the predewatering column. Condensate can be formed as early as in this stage.

The cooled product mixture is fed to a distillation column (3) which is equipped with packing elements instead of trays (predewatering column). As packing elements, it is possible to use the packing elements customary in chemical process engineering, for example packing elements made of metallic or ceramic materials or of plastic. Preference is given to metallic materials. Examples of metallic materials are iron, for example steel, in particular stainless steel, copper, brass, aluminum, nickel, Monel metals or titanium. Examples of ceramic materials are oxides of the main group metals or semimetals, for example of boron, aluminum or silicon, in particular borosilicate glasses or aluminosilicate glasses. Examples of plastics are polyolefins, halogen-substituted polyolefins, polyether sulfones, polyphenylene sulfides or polyaryl ether ketones. The packing elements can be present in various shapes, for example in hollow cylinder form, also referred to as rings, saddle form or spherical form. Preference is given to Pall rings, Berl saddles, Hiflow rings, Intalox saddles, Igels or in particular Raschig super rings. The packing elements have one or more diameters of preferably from 5 to 100 mm, particularly preferably from 10 to 80 mm and most preferably from 25 to 50 mm. The packing elements have a specific surface area of preferably from 80 to 350 $m^2/m^3$ and particularly preferably from 100 to 250 $m^2/m^3$. The specific surface area is obtained by multiplying the surface of the material of which a packing element is made by the number of these packing elements, based on one cubic meter of the bed.

The packing elements can be used as ordered packing or preferably as bed. In a bed, a large number of packing elements are, as is known, present in a loose and disordered layer on support elements such as perforated support gratings or other support trays or gratings. To fix the beds of packing elements in place, the column can be equipped with a holding-down grating at the upper end of the bed. When a plurality of support elements are used, a number of layers of packing elements can be installed (layers). Ordered packings have a regularly shaped structure, for example woven mesh or sheet metal packings, in particular thin, corrugated or perforated plates or meshes, for example composed of metal, plastic, glass or ceramic. The respective process gas flows as usual through the bed or ordered packing. The ordered packings have a specific surface area of preferably from 100 to 750 $m^2/m^3$ and particularly preferably from 150 to 350 $m^2/m^3$. The specific surface area is given by the surface area of the material of which the packing is made, based on one cubic meter of the packing. Goodloe packings, i.e. packings made of rolled VA wire mesh, are preferably not used.

In general, the predewatering column (3) on an industrial scale has a diameter of from 2 m to 6 m, preferably from 3 m to 5 m. In general, the predewatering column (3) is equipped with from one to four ordered packings or from one to four beds, preferably from two to three ordered packings or from two to three beds, each having a height of from 2 m to 12 m, preferably from 5 m to 9 m.

The predewatering column is preferably operated with a number of theoretical plates for the acetic acid and ethyl acetate removal of at least 5, preferably at least 10, even more preferably at least 13, and it should be taken into account in designing the height of the column that the HETP values (HETP=Height Equivalent to a Theoretical Plate) are greatly increased by the high proportion of inert gas in the gas phase (ethylene).

The predewatering column (3) can be heated and is preferably operated without additional heating. At the top of the predewatering column (3), the overhead product containing essentially water, vinyl acetate and ethylene is cooled to preferably from 10° C. to 35° C., particularly preferably from 10° C. to 30° C., by means of heat exchange in one or more heat exchangers (4). The condensate obtained (overhead product condensate) can be cooled in a dedicated heat exchanger (4) and is separated in a phase separator (5) into an aqueous phase and an organic phase containing essentially vinyl acetate (vinyl acetate phase).

The column is operated in such a way that the acetic acid present in the product mixture is separated off to an extent of at least 99% by weight, preferably to an extent of from 99.9 to 100% by weight, via the bottom of the predewatering column (3) and that the overhead product from the predewatering column contains <0.1% by weight of acetic acid, preferably <0.01% by weight of acetic acid, most preferably from 20 to 50 ppm by weight of acetic acid, in each case measured in the aqueous phase of the overhead product condensate which is taken off from the phase separator (5).

The ethyl acetate present in the product mixture is separated off via the bottom of the predewatering column (3) in such an amount that the overhead product from the predewatering column contains ≤600 ppm by weight of ethyl acetate, preferably from 100 to 300 ppm by weight, in each case measured in the vinyl acetate phase of the overhead product condensate.

The vinyl acetate phase can be recirculated, with or without further heating by means of one or more heat exchangers, for example with heat integration with the vapor stream exiting from the column, to the predewatering column (3). The vinyl acetate phase is preferably recirculated without further heating to the predewatering column (3). The liquid vinyl acetate phase is preferably fed in at the top of the predewatering column (3). The separation performance of the predewatering column (3) is controlled in a manner known to those skilled in the art via the temperature of the product mixture on entry into the predewatering column (3), via the recycle gas exit temperature after condensation by means of the heat exchangers (4) and via the amount of runback of vinyl acetate phase from the phase separator (5) into the predewatering column (3). In general, the vinyl acetate phase is recirculated to an extent of from 70 to 100% by weight, preferably to an extent of from 85 too 100% by weight, into the predewatering column (3). The remainder can optionally be fed into a dewatering column in which the vinyl acetate/water mixture from the azeotrope column is fractionated.

The uncondensed components of the overhead product from the predewatering column (3), essentially ethylene, carbon dioxide and vinyl acetate, are fed to the recycle gas scrubber (7). Here, the recycle gas exit temperature from the heat exchangers (4) above the dew point determines the amount of vinyl acetate which goes to the recycle gas scrubber. There, the uncondensed vinyl acetate is absorbed by means of acetic acid and removed from the recycle gas.

The recycle gas, or at least part thereof, can then be freed of carbon dioxide formed in a $CO_2$ scrubber ($CO_2$ absorption/desorption). The acetic acid used for the recycle gas scrub can, for example, be supplied from the azeotrope column and/or from the residue work-up. The bottom product from the recycle gas scrubber (7) can optionally be recirculated in its entirety or in part to the predewatering column (3). The acetic acid-containing water stream from a water scrubber upstream of the $CO_2$ scrubber ($CO_2$ absorption/desorption) can optionally be recirculated in its entirety or in part to the predewatering column (3). The recycle gas which is now free of vinyl acetate after the recycle gas scrubber and $CO_2$ scrubber can be fed via a recycle gas compressor and an acetic acid saturator back to the reaction in the reactor.

The bottom product from the predewatering column (3), which contains from 10 to 60% by weight, preferably from 30 to 50% by weight, vinyl acetate, can be collected in a collection vessel (6), namely the crude vinyl acetate vessel, and be fractionated further in a further distillation column, namely the azeotrope column. In the azeotrope column, the acetic acid which can be returned as recycled acetic acid to the recycle gas is obtained at the bottom. The ethyl acetate can be discharged via a side offtake to the ethyl acetate column in order to remove the ethyl acetate. At the top of the azeotrope column, a mixture containing water and vinyl acetate is obtained and this can be fractionated in the dewatering column.

After phase separation into an aqueous phase and a vinyl acetate phase, the vinyl acetate can be dewatered in a dewatering column and be isolated in a pure vinyl acetate column. The aqueous phase can be treated together with further aqueous phases from the process, for example the aqueous phase from the phase separator (5) downstream of the predewatering column (3), in a wastewater column.

Surprisingly, the separation performance of the predewatering column (3) remained approximately the same with the change from trays to packing elements (revamp), i.e. at the same column diameter and the same column height. This was unexpected because two liquid phases, namely a vinyl acetate/acetic acid phase and an aqueous phase, come into contact with one another in the predewatering column (3). In the case of two liquid phases in three-phase rectification, it is generally expected that the separation performance would be better in a tray column because of the permanent mixing of the liquid phases there. For this reason, predominantly tray columns are used in the field of three-phase rectification in the industry. Columns with ordered packing or random packing elements are not employed in a targeted manner in this field since the behavior of the separation performance (decrease in separation performance as a result of demixing of the two liquid phases) and handling the two liquid phases in the distributors has not been clarified.

With the conversion (revamp) of a tray column as predewatering column (3) to a packed column, the amount of recycle gas in a plant was able to be increased by 25%, measured upstream of the acetic acid saturator and downstream of the addition of ethylene, on the industrial scale of the same column diameter and the same column height and the capacity of a plant could be increased by almost 20% from 170 000 metric tons per year to 200 000 metric tons per year of vinyl acetate since the premature flooding of the tray column (presumably due to foam formation) above a particular amount of recycle gas could be reduced by equipping the column with packing elements.

A further advantage was that the residence time of vinyl acetate in the column is reduced since significantly less liquid holdup is present in the column and the degradation of vinyl acetate due to reverse reaction (hydrolysis to acetaldehyde and acetic acid) is therefore also reduced. The result was an increase in the yield of vinyl acetate by 1% by weight at the same usage of starting material. In the case of an industrial plant having a capacity of 200 000 metric tons per year of vinyl acetate, this is an additional 2000 metric tons of vinyl acetate per year.

In the process of the invention, in which the product mixture leaving the reactor is cooled before entering the predewatering column (3), the proportion of vinyl acetate in the bottoms from the predewatering column (3) is also increased. In the case of the processes known from the prior art, it was surprisingly observed that more vinyl acetate than would be possible according to the dew point goes to the recycle gas scrubber (7). Aerosol problems at the top of the predewatering column (3), as a result of which additional vinyl acetate is carried out as very fine droplets (aerosols) after the heat exchangers (4) to the recycle gas scrubber (7), are presumed. In the process of the invention, these aerosol problems could be reduced since, at the same recycle gas exit temperature from the heat exchangers (4), less vinyl acetate arrives at the recycle gas scrubber (7), and more vinyl acetate is then present in the bottom product from the predewatering column (3). As a consequence, less vinyl acetate, had to be removed from the gas phase in the recycle gas scrubber. This led to a significantly decreased load on the recycle gas scrubber.

The pressure drop in the predewatering column was also able to be reduced by means of the packing elements, which in turn decreases the load on the recycle gas compressor and led there to a significant reduction in the power consumption.

The limiting of the proportion of acetic acid in the overhead product from the predewatering column maintains and increases the miscibility gap between water and vinyl acetate in the phase separator, which ensures sharp separation of these constituents. The limiting of the proportion of vinyl acetate to <600 ppm in the overhead product from the predewatering column prevents discharge of ethyl acetate via the recycle gas stream, which helps to avoid complicated measures for decreasing ethyl acetate in the pure vinyl acetate.

The invention claimed is:

1. A process for preparing vinyl acetate by a heterogeneously catalyzed, continuous gas-phase reaction of ethylene, acetic acid and oxygen in a reactor, where the product mixture leaving the reactor is fractionated by means of distillation, the reaction products vinyl acetate and water and unreacted acetic acid are at least partly condensed out from the product mixture (recycle gas) and the recycle gas which has been treated in this way is recirculated back into the reactor, comprising
   a) cooling a gaseous product mixture leaving the reactor to a temperature of from 100° C. to 120° C. by one or more heat exchangers,
   b) feeding the resulting product mixture to a predewatering column equipped with packing elements and has a diameter of from 2 m to 6 m and is equipped with from one to four ordered packings or from one to four beds each having a height of from 2 m to 12 m,
   c) cooling an overhead product containing essentially water, vinyl acetate and ethylene from the predewatering column obtaining an overhead product condensate, the overhead product condensate is separated in a phase separator into an aqueous phase and an organic phase containing essentially vinyl acetate (vinyl acetate phase),
   d) separating off acetic acid present in the product mixture to an extent of at least 99% by weight via the bottom of the predewatering column and the overhead product from the predewatering column contains <0.1% by weight of acetic acid, measured in the aqueous phase of the overhead product condensate,
   e) separating off ethyl acetate present in the product mixture via the bottom of the predewatering column in such an amount that the overhead product from the predewatering column contains <600 ppm by weight of ethyl acetate, measured in the vinyl acetate phase of the overhead product condensate,
   f) recirculating the vinyl acetate phase to an extent of from 70 to 100% by weight into the predewatering column and
   g) taking off a product mixture containing from 10 to 60% by weight of vinyl acetate at the bottom of the predewatering column.

2. The process of claim 1, wherein the overhead product from the predewatering column contains <0.01% by weight of acetic acid, measured in the aqueous phase of the overhead product condensate.

3. The process of claim 2, wherein the overhead product from the predewatering column is cooled to from 10° C. to 35° C.

4. The process of claim 3, wherein the recycle is fed into a recycle gas scrubber and a bottom product from the recycle gas scrubber is recirculated in its entirety or in part to the predewatering column.

5. The process of claim 4, wherein the recycle gas after the treatment in the recycle gas scrubber is freed of carbondioxide formed in a CO2 scrubber and in that the acetic acid-containing water stream from a water scrubber upstream of the CO2 scrub (CO2 adsorption/desorption) is recirculated in its entirety or in part to the predewatering column.

* * * * *